US008067430B1

(12) United States Patent
Ugen et al.

(10) Patent No.: US 8,067,430 B1
(45) Date of Patent: Nov. 29, 2011

(54) ANTI-HIV ACTIVITY OF THE OPIOID ANTAGONIST NALOXONE

(75) Inventors: Kenneth E. Ugen, Tampa, FL (US); Steven Specter, Tampa, FL (US); Susan B. Nyland, Hershey, PA (US); Chuanhai Cao, Tampa, FL (US)

(73) Assignee: University of South Florida, Tampa, FL (US)

( * ) Notice: Subject to any disclaimer, the term of this patent is extended or adjusted under 35 U.S.C. 154(b) by 1363 days.

(21) Appl. No.: 10/902,471

(22) Filed: Jul. 29, 2004

Related U.S. Application Data

(60) Provisional application No. 60/481,156, filed on Jul. 29, 2003.

(51) Int. Cl.
*A61K 31/485* (2006.01)
(52) U.S. Cl. ...................................... 514/282
(58) Field of Classification Search ................... 514/282
See application file for complete search history.

(56) References Cited

U.S. PATENT DOCUMENTS

| | | | | |
|---|---|---|---|---|
| 4,546,103 | A * | 10/1985 | Huebner | 514/282 |
| 4,888,346 | A * | 12/1989 | Bihari et al. | 514/282 |
| 2003/0069263 | A1* | 4/2003 | Breder et al. | 514/282 |
| 2003/0105121 | A1* | 6/2003 | Bihari | 514/282 |

OTHER PUBLICATIONS

De Clercq, Eric. "New Developments in anti-HIV chemotherapy". Biochimica et Biophysica Acta. 2002. vol. 1587. pp. 258-275.*
Schmidt, William K. "Alvimopan (ADL 8-2698) is a Novel Peripheral Opioid Antagonist". The American Journal of Surgery. 2001. vol. 182, Suppl to Nov. 2001). pp. 27S-38S.*
Suzuki et al, Methadone induces CCR5 and promotes AIDS virus infection, FEBS Letters, 519 , 2002, pp. 173-177.*
Medicine.net (Definition of HTLV-III, retrieved from the internet on May 14, 2010, HTML: http://www.medterms.com/script/main/art.asp?articlekey=38558.*
Schafer et al. Drug Discovery Today 2008, 13 (21/22), 913-916.*
Horig et al. Journal of Translational Medicine 2004, 2(44).*
Ando et al.(Remington: The science and practice of pharmacy, 20th Edition, pp. 704-712).*
Gekker, Ganya et al., Naltrexone Potentiates Anti-HIV-1 Activity of Antiretroviral Drugs in CD4+ Lymphocyte Cultures, Drug and Alcohol Dependence, 2001, 257-263, vol. 64.
Ho, Wen-Zhe et al., Methylnaltrexone Antagonizes Opioid-Mediated Enhancement of HIV Infection, The Journal of Pharmacology and Exp. Therapeutics, 2003, 1158-1162, 307(3).
Gekker, G. et al. Jun. 2002. "Naloxone Potentiates Anti-HIV-1 Activity of Antiretroviral Drugs in CD4+ Lymphocyte Cultures." International Journal of Infectious Diseases. vol. 6. Suppl. 2. pp. S14-S15.
Gekker, G. et al. Jan. 2001. "Naltrexone Potentiates Anti-HIV-1 Activity of Antiretroviral Drugs in CD4+ Lymphocyte Cultures." Drug and Alcohol Dependence. vol. 64. pp. 257-263.
Brown et al. 2009. "Low-Dose Naltrexone for Disease Prevention and Quality of Life." Medical Hypotheses. vol. 72. No. 3. pp. 333-337.
Wang et al. 2007. "Diffrerent Effects of Opioid Antagonists on Mu-, Delta-, and Kappa-Opioid Receptors With and Without Agonist Pretreatment." The Journal of Pharmacology and Experimental Therapeutics. vol. 321. No. 2. pp. 544-552.

(Continued)

*Primary Examiner* — Jeffrey S Lundgren
*Assistant Examiner* — Savitha Rao
(74) *Attorney, Agent, or Firm* — Michele L. Lawson; Smith & Hopen, P.A.

(57) ABSTRACT

A method of treating HIV infection by using the novel anti-HIV activity of the opioid antagonist naloxone.

2 Claims, 4 Drawing Sheets

OTHER PUBLICATIONS

Peng et al. 2007. "Pharmacological Properties of Bivalent Ligands Containing Butorphan Linked to Nalbuphine, Naltrexone, and Naloxone at Mu, Delta, and Kappa Opioid Receptors." J. Med. Chem. vol. 50. pp. 2254-2258.

* cited by examiner

FIGURE 1 A-D
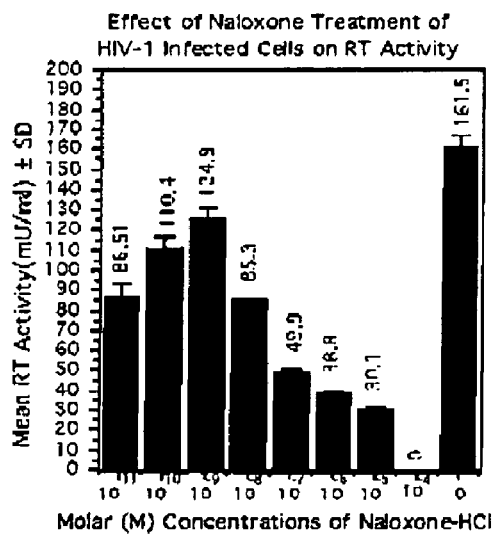
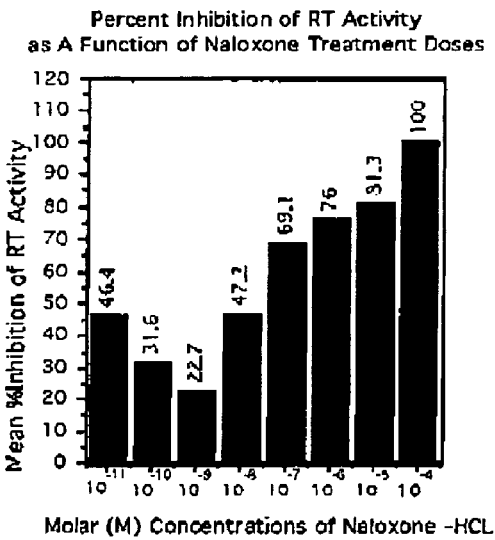
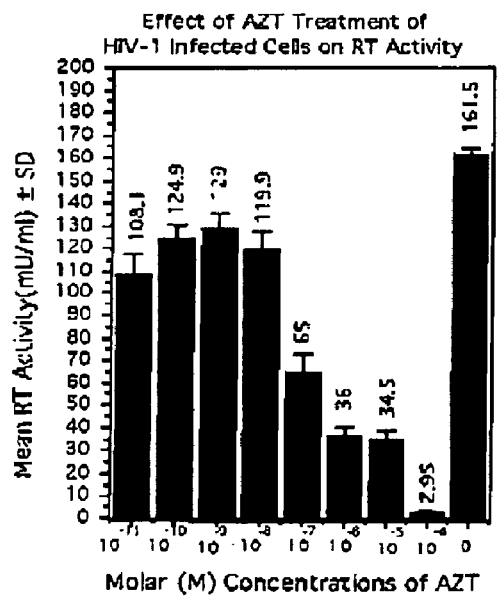
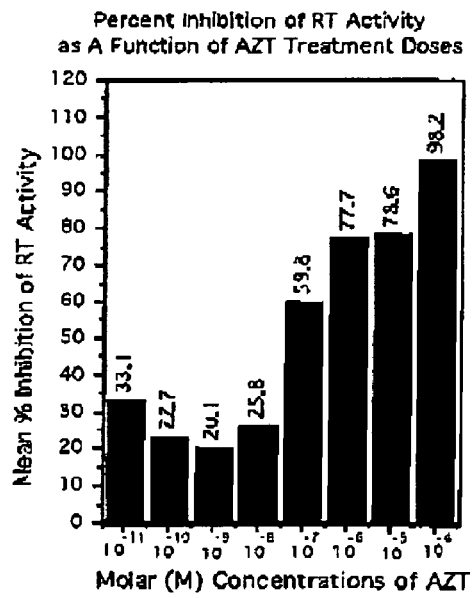
RT = reverse transcriptase (activity measured as milliunits/ml)
AZT = azidothymidine (zidovudine)
mU/ml = milliunits/ml
SD = standard deviation FIGURE 2A and B
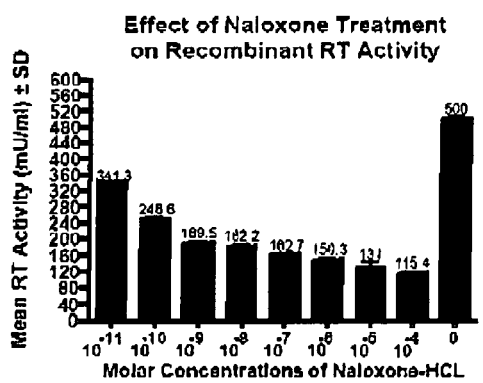
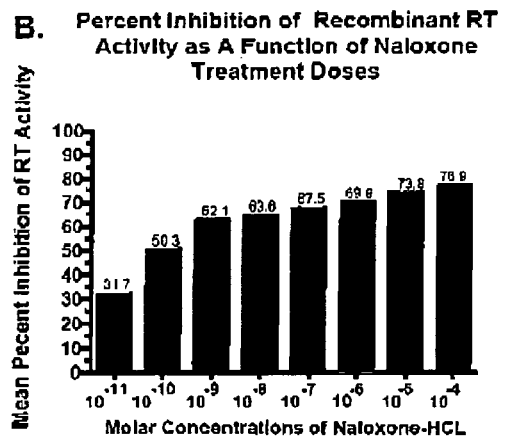
Key:
RT = reverse transcriptase
mU/ml = milliunits/ml
Individual value labels are shown above each bar Effect of naloxone or AZT treatment of HIV-1 infected on gp120 expression Key:
Std = protein molecular weight standard of 98KD in size RT-PCR amplification of HIV-1gp41 (prominent white bands in each lane) from HIV-MN infected SupT1 cells treated with naloxone at a range of molar concentrations.

VC = virus control (no treatment with drug)
CC = cell control (cells not infected with HIV-1)
Marker = DNA molecular weight markers of different sizes

ANTI-HIV ACTIVITY OF THE OPIOID ANTAGONIST NALOXONE

CROSS REFERENCE TO RELATED APPLICATIONS

This application claims priority to U.S. Provisional Patent Application No. 60/481,156 of the same title and by the same inventors, filed Jul. 29, 2003.

GOVERNMENT SUPPORT

National Research Service Award (NRDA)—Grant No. DA05913.

BACKGROUND OF THE INVENTION

The pandemic of AIDS (Acquired Immunodeficiency Syndrome) represents one of the greatest challenges faced by biomedical science. Although AIDS has been kept in check, to a certain degree, in the U.S. through the use of antiretroviral therapy, infections still occur and not all Americans have access to appropriate therapies. In other parts of the world, particularly Africa, AIDS is devastating with infections occurring at an unchecked rate. In addition, in those infected regions, sophisticated antiretroviral therapy is not available which often results in high and often rapid mortality.

Short of the availability of an effective vaccine it is absolutely essential to develop new, effective and economical drug therapies. This is particularly important because of the ability of the human immunodeficiency virus (HIV), the causative agent for AIDS, to become resistant to some effective therapies.

One of the problems with the generation of new drug therapies against HIV is the development of resistance by the virus to the therapy. Unfortunately, the development of resistance has become a serious problem with AZT (zidovudine). Resistant viruses are also developing against the newer protease inhibitor drug therapies. With the development of resistance it is critical to continually develop new drug therapies against HIV. Therefore, what are needed are novel efficacious drug therapies for the treatment of HIV infection and AIDS.

SUMMARY OF INVENTION

This invention describes the discovery of novel anti-HIV activity for naloxone hydrochloride, NARCAN, which is currently used to treat opioid abuse (morphine, heroin, etc.).

In one embodiment the inventive method provides for the treatment of a patient, infected with a virus, comprising the step of administering to the patient a therapeutically effective amount of an opioid antagonist. The target virus is the human immunodeficiency virus (HIV) and the opioid antagonist is naloxone hydrochloride.

In another embodiment, provided is a method of inhibiting reverse transcriptase activity in a cell infected with the human immunodeficiency virus (HIV) comprising the step of contacting the infected with a therapeutically effective amount of naloxone hydrochloride.

Another embodiment of the present invention includes a method of modulating the expression of a coat protein of a virus comprising the step of contacting the virus with a therapeutically effective amount of naloxone hydrochloride, wherein the coat protein of the virus is chosen from the group consisting of gp41 and gp120.

In yet another embodiment, provided is an antiviral compound comprising an opioid antagonist, wherein the opioid antagonist is naloxone hydrochloride.

BRIEF DESCRIPTION OF THE DRAWINGS

For a fuller understanding of the nature and objects of the invention, reference should be made to the following detailed description, taken in connection with the accompanying drawings, in which:

FIG. 1 (A-D) shows the results of the differential effect of a range of molar concentrations of naloxone or AZT on reverse transcriptase activity in HIV infected cells:

FIG. 1A shows the RT activity in HIV-MN infected Supt 1 cells treated with different molar concentrations of naloxone. The data demonstrate that as the treatment dose of naloxone increases from $10^{-11}$ to $10^{-4}$ M RT activity decreases. The column in the graph labeled 0 is the control (i.e. no drug treatment).

FIG. 1B shows the % decrease in RT activity for the different treatment doses compared to the RT activity in the control.

FIGS. 1C and 1D show results from the treatment of HIV-MN infected Supt 1 cells with an identical molar dose range of the established anti-HIV drug AZT.

FIGS. 2A and 2B summarize the results of the effect of different molar concentrations of naloxone on recombinant RT (that is, protein not within the HIV viral lysate). Analogous to the effects on RT in HIV, naloxone demonstrated a direct inhibitory effect on RT.

DETAILED DESCRIPTION OF THE PREFERRED EMBODIMENT

Figure 3:
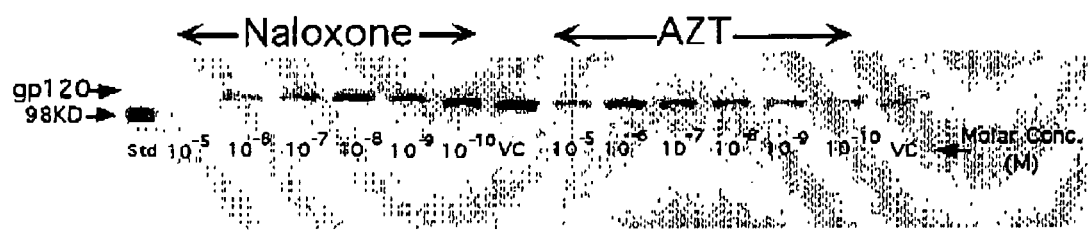
FIG. 3 shows the immunoblot (Western blot) results using lysates from HIV infected Supt 1 cells that had been treated with different molar concentrations of either AZT or naloxone. The expression of the essential HIV coat protein gp120 is measured by this technique. Western Blot analysis of gp120 detected with a murine anti-gp120 monoclonal antibody from HIV-1 infected cells treated with naloxone or AZT. HIV-MN infected Supt 1 cells treated will different molar concentrations of naloxone or AZT. Cells were lysed at 3 days after infection of the cells with cell free HIV-1MN and 100 μg of the lysate was loaded onto SDS-PAGE, transferred onto a Hybond ECL membrane and detected with an anti-gp120 monoclonal antibody. VC=viral control (infected cells with no drug treatment).

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Administering or Contacting—as used herein refers to the process of delivering to a cell, ex vivo, or a host, in vivo, a therapeutic substance, or a combination of several therapeutic substances. The process can include any method known in the art and is dependent on the type of substance or substances administered. Possible methods include, but are not limited to, parenteral (i.e. subcutaneously, intravenously, intramuscularly, intra-arterially, and direct injection into a tissue or organ), mucosal (i.e. intranasally), pulmonary (i.e. via inhalation), topical, via catheter (i.e. iontopheretically) or orally. Administration is usually achieved via a pharmaceutically acceptable carrier.

CCR-5—as used herein refers to the protein encoded by the gene for CCR5 which is located on chromosome 3 in the p21.3-p24 region. CCR5 is a chemokine receptor present in different cells, especially in macrophages, monocytes, and T cells, where it acts as a co-receptor for HIV-1 in these cells. Chemokines and their receptors are believed to be involved in the inflammatory response, mediating leukocyte movement and activation.

CD4—as used herein refers to a T-cell receptor protein which interacts with and recognizes major histocompatibility complex proteins. CD4 is the receptor for the human immunodeficiency virus (HIV) and may mediate its entry into the host cell. It has a high affinity for the envelope protein of HIV, gp160, and also for its split product, gp120.

gp120—as used herein refers to glycoprotein 120, a protein that protrudes from the surface of HIV and binds to CD4+ T cells. In a two-step process that allows HIV to breach the membrane of T cells, gp120-CD4 complex refolds to reveal a second structure that binds to CCR5, one of several chemokine co-receptors used by the virus to gain entry into T cells.

gp41—as used herein refers to glycoprotein 41, a protein embedded in the outer envelope of HIV. gp 41 plays a key role in HIV's infection of CD4+ T cells by facilitating the fusion of the viral and the cell membranes.

Therapeutically Effective Amount—as used herein is that amount of a substance necessary to achieve a desired therapeutic result. For example, if the therapeutic result desired is the enhanced yield of stem cells, the therapeutically effective amount is that amount that facilitates, or achieves, an increase in the total number of stem cells in a given population. The therapeutically effective amount can be a dosage administered in at least one amount and can include an administration protocol spanning several days or weeks.

This inventive method includes the use of the novel anti-HIV activity of naloxone hydrochloride (NARCAN), a narcotic antagonist, to treat patients infected with HIV. The medical indication for this drug is the treatment and partial, or total, reversal of the effects of opioid abuse. That is, naloxone is a competitive narcotic antagonist used in the management and reversal of overdoses caused by narcotics and synthetic narcotic agents. Unlike other narcotic antagonists, which do not completely inhibit the analgesic properties of opiates, naloxone antagonizes all actions of morphine.

Naloxone's Effect on Reverse Transcriptase Activity

Many studies have dealt with the effects of opioids (morphine and analogs) on infection of cells by pathogenic human retroviruses (HIV and another retrovirus called the human T cell leukemia virus (HTLV)). In these experiments it may be necessary to antagonize the effect of the opioids with an antagonist, in order to confirm the specificity of any effect by the opioids. Here, the opioid antagonist naloxone (NARCAN) was chosen. Surprisingly, it was discovered in control experiments using antagonist alone that naloxone treatment exerted anti-HIV activity. This was indicated by a direct inhibitory effect by the drug on the reverse transcriptase (RT) enzyme activity of the virus. RT activity is essential for replication of the virus and ultimately the ability of the virus to infect cells. By comparison, the established anti-HIV drug AZT (zidovudine) inhibits HIV through its effect on RT. Importantly; initial analysis indicates that naloxone is at least as effective as AZT in inhibiting RT activity at similar concentrations. This was determined by measuring, in the same experiment, the effects of AZT or naloxone (at identical molar concentrations) on RT activity.

Naloxone's Effect on Retrovirus Binding Activity

In addition to having a direct effect on RT activity the ability of naloxone to inhibit HIV was measured through the determination of expression of critical coat proteins of HIV (called gp41 and gp120). This was accomplished either through RT-PCR (reverse transcriptase-polymerase chain reaction) which measures messenger RNA (mRNA) and by immunoblotting (Western blotting) which directly measures the expression of protein. Naloxone treatment of HIV infected lymphocytes was able to significantly depress expression of these necessary proteins through measurement of mRNA and protein expression.

Example 1

Cell Infection by HIV and Sample Preparation for Analysis

200TCID-50 per milliliter (tissue culture infectious dose) of HIV-MN cell free virus was used to infect 500,000/milliliter of a human T cell line (called SupTI) in the presence (at a range of concentrations) or absence (control) of naloxone-HC1/or AZT. The TCID-50 is an amount of virus which will infect 50% of non-infected target cells. The virus+cells+drugs (naloxone or AZT) were incubated at 37 degrees Celsius in an atmosphere of 5% carbon dioxide for three days. Cells were lysed by using a detergent 1% Triton-X100. This preparation was frozen in liquid nitrogen and thawed at 37 degrees Celsius for three cycles. The preparation was vortexed vigorously for 20 seconds at the end of each cycle. Samples were then stored at −80 degrees Celsius until analysis. Total RNA from the samples were prepared by using the Tri-reagent assay and aliquoted and stored at −80 degrees Celsius until RT-PCR (reverse transcriptase-polymerase chain reaction) analysis.

Example 2

RT (Reverse Transcriptase) Activity Assay (Used to Measure Effect of Drug Treatments on HIV Infected Cells)

A 96 well microplate was coated with 200 µl/well of a 40 mg/ml solution of polyA and incubated at room temperature overnight with rocking. The plate was then washed 3× with TBS (Tris buffered saline, pH 7.8) 100 µl/well of either lysed experimental samples (from infected drug treated cells) or RT standards were added to the wells followed by the addition of 60 µl/well of RT buffer. This was followed by the addition of 40 µl/well of a nucleotide mix. The reaction mixture was then incubated at 37 degrees Celsius for 40 min. The plates were then washed 3× with TBS followed by the addition of anti-DIG-POD-HRP (a specific antibody against RT which allows for the accurate measurement of this enzyme) at a dilution of 1:5000 in TGSE (a 10 mM pH 7.5 Tris buffer containing 1% gelatin and 1 mM sodium EDTA) buffer at 100 Owen and incubated for 1 hour at 37 degrees Celsius. Plates were then washed 6× with TBS followed by the addition of 100 µl/well of a soluble substrate for HRP designated TMB (tetra-methyl benzidine) in perborate buffer. Color development, due to the reaction of the substrate with the enzyme (HRP) conjugate was allowed to occur at room temperature for 15 min. The colorimetric reaction was stopped by the addition of 25 µl/well of 2 molar sulfuric acid. The color reaction in the wells was measured spectrophotometrically. Color development was proportional to the amount of RT in the wells and quantitation was made based upon a standard curve of using recombinant RT. FIG. 1 (A-D) shows the results of the differential effect of a range of molar concentrations of naloxone or AZT on reverse transcriptase activity in HIV infected cells. Specifically, FIG. 1A shows the RT activity in HIV-MN infected Supt 1 cells treated with different molar concentrations of naloxone. The data demonstrate that as the treatment dose of naloxone increases from $10^{-11}$ to $10^{-4}$ M RT activity decreases. The column in the graph labeled 0 is the control (i.e. no drug treatment). FIG. 1B shows the % decrease in RT activity for the different treatment doses compared to the RT activity in the control. FIGS. 1C and 1D show results from the treatment of HIV-MN infected Supt 1 cells with an identical molar dose range of the established anti-HIV drug AZT. Accordingly, naloxone is at least as effective as AZT in inhibiting RT activity in HIV infected cells.

FIGS. 2A and 2B summarize the results of the effect of different molar concentrations of naloxone on recombinant RT (that is, protein not within the HIV viral lysate). Analogous to the effects on RT in HIV, naloxone demonstrated a direct inhibitory effect on RT. Therefore, it can be seen that naloxone inhibits HIV through its effect on RT.

Example 3

RT-PCR (Reverse Transcriptase-Polymerase Chain Reaction)—(for Quantitation of Viral RNA as a Function of Treatment with the Drug Regimens)

Total RNA from the preparations described above was used as a template for the generation of complementary DNA (cDNA). This was accomplished through the use of commercial RT-PCR kits (Gibco/BRL/Life Technologies, Inc., Rockville, Md.). The gene for the HIV gp41 transmembrane envelope glycoprotein was amplified from the RT products through the use of the following PCR cycling conditions: 94 degrees Celsius for 2 minutes followed by 52 degrees Celsius for 1 minutes then followed by 32 cycles at 94 degrees Celsius for 1 minutes, 52 degrees Celsius for 1 minutes, 72 degrees Celsius for 15 minutes, then PCR extension was accomplished at 72 degrees Celsius for 10 minutes. The cycles were then ended by incubation at 4 degrees Celsius for 16 hours. 5 ml (microliters) of PCR products were then loaded onto a 1.5% agarose gel containing 5 µg/ml of ethidium bromide. Bands in the gel with a size of 1.2 kb was considered to be gp41 based upon the primers used in the assay: Primer Sequences are as follows: Sense: 5 prime-CAGCGATAG-GAGCTCTGTTCC-3 prime (SEQ ID NO:1); Antisense 5 prime-GACCATTTGCCACCCATCTTA-3 prime (SEQ ID NO:2). In order to eliminate the possibility that the drug treatments could have an inhibitory effect on the RT used in the RT-PCR reaction rather than the HIV RT a constitutive (i.e. always expressed) enzyme called GADPH was used as a control. No effect of drug treatment on expression of this enzyme was noted indicating that the RT used in the assay condition was not affected by the drug. That is GADPH can be considered a 'housekeeping' gene of the T cell which should have the same level of expression under all the drug treatment conditions. The lack of an effect on GADPH also proves that there was no residual drug (naloxone or AZT) present in the RNA sample used for analysis. The primer sequence used for GADPH were as follows: sense 5 prime-GGTGAAGGTCGGAGTCAACGGA-3 prime (SEQ ID NO:3); antisense 5 prime-GAGGGATCTCGCTCCTGG-GAAGA-3 prime (SEQ ID NO:4). The absence of or a decreased intensity of the gp41 band from infected cells treated with the drugs compared to control (non-treated) is indicative of an inhibitory effect of the drug treatment on HIV.

Figure 4:
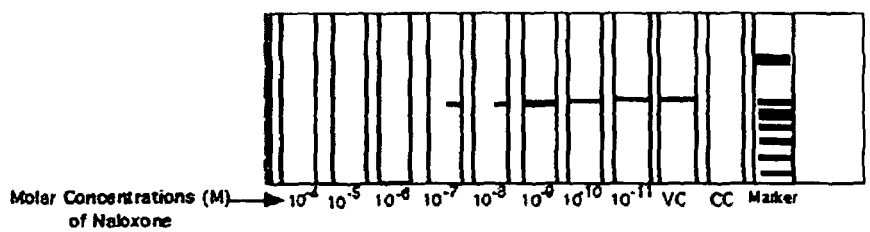
FIG. 4 is a RT-PCR analysis of RNA from HIV infected target cells which had been treated with different molar concentrations of naloxone. The expression of the critical coat protein gp41 is being measured by this molecular analysis.

FIG. 4 is a RT-PCR analysis of RNA from HIV infected target cells which had been treated with different molar concentrations of naloxone. The expression of the critical coat protein gp41 is measured by this molecular analysis. As shown in FIG. 4, naloxone inhibits HIV at the molecular level by inhibiting expression of RNA for the envelope glycoprotein gp41.

Example 4

Immunoblot (Western Blot) Assay (for Quantitation of Viral Protein Expression as a Function of Treatment with the Drug Regimens)

100 mg of protein lysate (i.e. from the HIV infected cells) from the samples described above were loaded onto a SDS-PAGE (sodium dodecyl sulfate-polyacrylamide gel electrophoresis) and then transferred to a hybond ECL membrane (considered the blot). This blot was probed, following an ECL kit protocol (Amersham Phamarcia, Inc.), with a mouse anti HIV-1 gp120 (external envelope glycoprotein). Binding of the mouse monoclonal antibody to the gp120 immobilized in the blot was detected by an anti-mouse HRP (horseradish peroxidase)/substrate similar to the one described above. The absence of or a decreased intensity of the gp120 band from infected cells treated with the drugs compared to control (non-treated) is indicative of an inhibitory effect of the drug treatment on HIV.

FIG. 3 shows the immunoblot (Western blot) results using lysates from HIV infected Supt 1 cells that had been treated with different molar concentrations of either AZT or naloxone. The expression of the essential HIV coat protein gp120 is measured by this technique. Thus, naloxone has been shown to be as effective, or more effective, than equivalent molar concentrations of AZT in inhibiting HIV as measured by expression of the HIV envelope glycoprotein.

There are several ways to quantify the activity of antiviral drugs. A direct method requires the ability to directly detect and measure a suitable biological endpoint. Indirect measures include the effects of the drug on the expression of viral messenger RNA or protein necessary for infectivity at the gene and/or protein. As for anti-HIV drugs, most recognized methods used are the measurement of HIV-I protein level indicated by p24 (HIV-1 core antigen) levels, RT (reverse transcriptase) activity, and immunoblot (i.e. Western) method. The method for measurement of messenger RNA level is RT-PCR (reverse transcriptase-polymerase chain reaction). Any measured changes in the parameters and methods of measurement listed above can indicate an inhibitory or stimulatory effect of the drug treatment Although AZT has been a somewhat effective anti-HIV drug used in the clinical treatment of AIDS patients, it has become limited because of the development of resistance to this drug by the virus. Researchers worldwide have been trying to find new drugs to counter this resistance problem. Here, it has been shown that the opioid antagonist naloxone can inhibit HIV replication.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

What is claimed is:

1. A method of inhibiting reverse transcriptase activity in a cell infected with the human immunodeficiency virus (HIV) comprising the step of contacting the infected cell with a solution consisting of naloxone hydrochloride having a molar concentration between $10^{-4}$ M and $10^{-11}$ M.

2. A method of modulating the expression of a coat protein of a human immunodeficiency virus comprising the step of contacting the virus with naloxone hydrochloride wherein the coat protein of the virus is chosen from the group consisting of gp41 and gp120.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: artificial sequence
<220> FEATURE:
<223> OTHER INFORMATION: Sense Primer Sequence for Assay

<400> SEQUENCE: 1
cagcgatagg agctctgttc c                                              21

<210> SEQ ID NO 2
<211> LENGTH: 21
<212> TYPE: DNA
<213> ORGANISM: artificial sequence
<220> FEATURE:
<223> OTHER INFORMATION: Antisense primer sequence for assay

<400> SEQUENCE: 2
gaccatttgc cacccatctt a                                              21

<210> SEQ ID NO 3
<211> LENGTH: 22
<212> TYPE: DNA
<213> ORGANISM: artificial sequence
<220> FEATURE:
<223> OTHER INFORMATION: Sense Primer sequence for GADPH

<400> SEQUENCE: 3
ggtgaaggtc ggagtcaacg ga                                             22

<210> SEQ ID NO 4
<211> LENGTH: 23
<212> TYPE: DNA
<213> ORGANISM: artificial sequence
<220> FEATURE:
<223> OTHER INFORMATION: Antisense Primer Sequence for GADPH

<400> SEQUENCE: 4
gagggatctc gctcctggga aga                                            23
```